(12) United States Patent
Murphy et al.

(10) Patent No.: US 7,416,602 B2
(45) Date of Patent: Aug. 26, 2008

(54) CALCIUM PHOSPHATE CEMENT

(75) Inventors: Matthew E. Murphy, Limerick (IE); Cillín P. Cleere, Limerick (IE); Brian J. Hess, Kalamazoo, MI (US); Gerard M. Insley, Raheen (IE)

(73) Assignee: Howmedica Leibinger, Inc., Portage, MI (US)

( * ) Notice: Subject to any disclaimer, the term of this patent is extended or adjusted under 35 U.S.C. 154(b) by 328 days.

(21) Appl. No.: 11/102,254

(22) Filed: Apr. 8, 2005

(65) Prior Publication Data

US 2006/0225620 A1 Oct. 12, 2006

(51) Int. Cl.
*C04B 12/02* (2006.01)
*A61K 6/00* (2006.01)

(52) U.S. Cl. .......................... 106/690; 106/35; 106/691

(58) Field of Classification Search ................ 106/35, 106/690, 691
See application file for complete search history.

(56) References Cited

U.S. PATENT DOCUMENTS

| | | | |
|---|---|---|---|
| 2,018,410 A | 10/1935 | McDonald | |
| 4,139,599 A * | 2/1979 | Tomlinson et al. | 423/308 |
| 4,244,931 A | 1/1981 | Jarvis et al. | |
| 4,312,843 A | 1/1982 | Monty et al. | |
| 4,472,365 A * | 9/1984 | Michel | 423/267 |
| 4,612,053 A | 9/1986 | Brown et al. | |
| 4,828,823 A * | 5/1989 | Li | 424/52 |
| 4,880,610 A | 11/1989 | Constantz | |
| RE33,161 E | 2/1990 | Chow | |
| RE33,221 E | 5/1990 | Brown et al. | |
| 4,973,168 A | 11/1990 | Chan et al. | |
| 5,024,825 A * | 6/1991 | Buhl et al. | 423/309 |
| 5,047,031 A | 9/1991 | Constantz | |
| 5,129,905 A | 7/1992 | Constantz | |
| 5,149,368 A | 9/1992 | Liu et al. | |
| 5,178,845 A | 1/1993 | Constantz et al. | |
| 5,262,166 A | 11/1993 | Liu et al. | |
| 5,336,264 A | 8/1994 | Constanz et al. | |
| 5,342,441 A | 8/1994 | Mandai et al. | |
| 5,427,756 A | 6/1995 | Dany et al. | |
| 5,522,893 A | 6/1996 | Takagi | |
| 5,525,148 A | 6/1996 | Chow | |
| 5,542,973 A | 8/1996 | Chow et al. | |
| 5,545,254 A | 8/1996 | Chow | |
| 5,569,442 A | 10/1996 | Fulmer et al. | |
| 5,605,713 A | 2/1997 | Boltong | |
| 5,697,981 A | 12/1997 | Ison et al. | |
| 5,709,742 A | 1/1998 | Fulmer et al. | |
| 5,782,971 A | 7/1998 | Constantz et al. | |
| 5,820,632 A | 10/1998 | Constantz et al. | |
| 5,900,254 A | 5/1999 | Constantz | |
| 5,952,010 A | 9/1999 | Constantz | |
| 5,962,028 A | 10/1999 | Constantz | |
| 5,968,253 A | 10/1999 | Poser et al. | |
| 6,002,065 A | 12/1999 | Constantz et al. | |
| 6,005,162 A | 12/1999 | Constantz | |
| 6,117,456 A | 9/2000 | Lee et al. | |
| 6,206,957 B1 | 3/2001 | Driessens et al. | |
| 6,375,935 B1 | 4/2002 | Constantz | |
| 6,379,453 B1 | 4/2002 | Lin et al. | |
| 6,409,972 B1 | 6/2002 | Chan | |
| 6,642,285 B1 | 11/2003 | Bohner | |
| 6,719,993 B2 | 4/2004 | Constantz | |
| 6,733,582 B1 | 5/2004 | Bohner et al. | |
| 6,793,725 B2 | 9/2004 | Chow et al. | |
| 6,929,692 B2 | 8/2005 | Tas | |
| 2002/0055143 A1 | 5/2002 | Bell et al. | |
| 2002/0155167 A1 | 10/2002 | Lee et al. | |
| 2003/0021824 A1 | 1/2003 | Lacout et al. | |
| 2003/0049329 A1 | 3/2003 | Lee et al. | |
| 2004/0244651 A1 | 12/2004 | Lemaitre et al. | |
| 2005/0074415 A1 | 4/2005 | Chow et al. | |
| 2005/0199156 A1 | 9/2005 | Khairoun et al. | |

FOREIGN PATENT DOCUMENTS

| | | | |
|---|---|---|---|
| EP | 0 627 899 | | 12/1994 |
| EP | 0 936 929 | | 8/1999 |
| EP | 1 237 585 | | 9/2002 |
| EP | 1 443 981 | | 8/2004 |
| WO | WO 93/16657 | * | 9/1993 |
| WO | WO-98/16268 A2 | | 4/1998 |
| WO | WO-00/07639 A1 | | 2/2000 |
| WO | WO-01/41824 A1 | | 6/2001 |
| WO | WO 03/041753 | * | 5/2003 |
| WO | WO-2004/000374 A1 | | 12/2003 |
| WO | WO-2005/009481 | | 2/2005 |
| WO | WO-2005/084726 | | 9/2005 |

OTHER PUBLICATIONS

Gbureck, Dembski, Thull, Barralet, "Factors influencing calcium phosphate cement shelf-life", Biomaterials, May 26, 2004.

Freche, M. & Heughebaert, J.C.; Calcium Phosphate Precipitation in the 60-80° C. Range, Journal of Crsytal Growth, vol. 94 (1989), pp. 947-954.

Komath, Varma and Sivakumar, "On the development of an apatitic calcium phosphate bone cement", Bull. Matter. Sci, vol. 23, No. 2, Apr. 2000, pp. 135-140.

Burguera, Guitian, Chow, "A water setting tetracalcium phosphate-dicalcium phosphate dihyrdrate cement", Wiley Periodicals, vol. 71A, No. 2, Oct. 2004.

Murphy, Clarkin & Insley, 'Calcium Phosphate Bone Cements of the Future: Towards the Understanding of their Chemistry', Biomaterials Research Group, Sep. 2005.

Chow et al., IADR Abstract No. 2410, Apr. 1991.

Chow et al., AADR Abstract, No. 666, 1992.

(Continued)

*Primary Examiner*—C. Melissa Koslow
(74) *Attorney, Agent, or Firm*—Lerner, David, Littenberg, Krumholz & Mentlik, LLP (57) ABSTRACT

The invention is related to a rapid setting calcium phosphate cement comprising a powdered first component comprising stabilized dicalcium phosphate dihydrous containing from about 10 ppm to about 60 ppm of magnesium, a powdered second component comprising a calcium phosphate mineral other than said stabilized dicalcium phosphate dihydrous, and a liquid third component comprising water.

38 Claims, 4 Drawing Sheets

OTHER PUBLICATIONS

Gisep, Kugler, Wahl, Rahn, 'Mechanical Characterization of a Bone Defect Model Filled with Ceramic Cements', J Mater Sci Mater Med, vol. 15, No. 10, pp. 1065-1071, Oct. 2004.

Jensen, Ooms, Verdonschot, Wolke, 'Injectable Calcium Phosphate Cement For Bone Repair and Implant Fixation', Orthop Clin North Am, vol. 36, No. 1, pp. 89-95, Jan. 2005.

Biotek, Inc., "Hydroformed Microspheres as New Injectable Drug Vehicle", Small Business Innovation Research (SBIR) Abstract Book, HHS, 1994.

Burguera EF, Xu HH, Weir MD, Injectable and rapid-setting calcium phosphate bone cement with dicalcium phosphate dihydrate, J Biomed Mater res B Appl Biomater, pp. 126-134 (2005).

Tofighi A, Mounic S, Chakravarthy P, Rey C, Lee D, "Setting Reactions Involved in Injectable Cements Based on Amorphous Calcium Phosphate", Key Engineering Materials, vol. 192-195, pp. 769-772, 2001.

Barralet, Grover, Gbureck, "Ionic Modification of Calcium Phosphate Cement Viscosity. Part II: Hypodermic Injection and Strength Improvement of Brushite Cement.", Biometerials, vol. 25, No. 11, pp. 2197-2203 (2004).

Gbureck, Barralet, Spatz, Grover, Thull "Ionic Modification of Calcium Phosphate Cement Viscosity. Part I: Hypodermic Injection and Strength Improvement of Apatite Cement.", Biometerials, vol. 25, No. 11, pp. 2187-2195 (2004).

Komath, Varma , "Development of a fully injectable calcium phosphate cement for Orthopedic and Dental Applications", Bull. Matter. Sci, Jun. 2003, pp. 415-422.

* cited by examiner

CALCIUM PHOSPHATE CEMENT

BACKGROUND OF THE INVENTION

The field of this invention pertains to calcium phosphate minerals for bone cement or bone filler applications and in the preparation of such cement. More specifically, this invention relates to a calcium phosphate bone cement comprising a mixture of tetra-calcium phosphate and di-calcium phosphate in an aqueous solution, in which the mixture then sets to form a bone cement with a substantial portion of the cement being hydroxyapatite.

Hydroxyapatite is the major natural building block of bone and teeth. It has been found useful in fixing fractures and bone defects to use bone cements which are formed by combining calcium and phosphate precursors in an aqueous solution which initially forms a paste but then hardens into a hydroxyapatite bone cement. Hydroxyapatite has a calcium-to-phosphorous ratio of approximately 1.67 which is generally the same as the calcium phosphate ratio in natural bone structures. The paste may be placed in situ prior to setting in situations where bone has been broken, destroyed, degraded, become too brittle or has been the subject of other deteriorating effects. Numerous calcium phosphate bone cements have been proposed such as those taught by Brown and Chow in U.S. Reissue Pat. No. 33,161 and 33,221, Chow and Takagi in U.S. Pat. 5,522,893, and by Constantz in U.S. Pat. Nos. 4,880,610 and 5,047,031, the teachings of these patents are incorporated herein by reference.

It has been well known since the initial use of calcium phosphate cements that the addition of sodium phosphate solutions, potassium phosphate solutions or sodium carbonate solutions to the aqueous setting solution of the calcium phosphate precursors can speed setting times. This is documented in the Chow et al., April, 1991 IADR Abstract No.: 2410 and AADR, 1992 Abstract No.: 666 and was known to those skilled in the art prior to these publications.

Typically, the powdered component, which may be a combination of tetracalcium phosphate and dicalcium phosphate is supplied in a sterile form in a blister pack or a bottle, e.g., with contents of 2 to 25 g. The liquid, e.g. a molar sodium phosphate solution, distilled water or sodium chloride solution is usually present in a sterile, glass container, usually a disposable syringe, having a volume of 10 cc. The powdered and liquid components are usually mixed in a vessel, and processed from this vessel, e.g., by means of a syringe or the like.

It is important that these components of bone cements have long-term stability during storage as these components may be stored for over weeks and months before the actual cement usage when the powdered component is mixed with the aqueous component to form a settable material. But, the long-term stability of these components have not been extensively studied because it has been assumed by those skilled in the art that they stay stable with little or no change in properties.

However, unlike the industry's general assumption, according to Gbirecl et al. in *Factors Influencing Calcium Phosphate Cement Shelf-life*, it has been found that some prior art powder mixtures of calcium phosphate lose their ability to set after 7 days of storage, despite being store in sealed containers. The deterioration of the prior art powder mixtures was subsequently found to be related to their conversion to monetite in a dry state during ageing.

Thus, there is a need to develop a rapid setting bone cement which overcomes the destabilization problems of the prior art. This need is fulfilled by the invention that is described herein.

SUMMARY OF THE INVENTION

It is an aspect of the invention to provide a rapid setting calcium phosphate bone cement with long-term shelf-life.

Furthermore, it is an aspect of the invention to provide a method for making a rapid setting bone cement with long-term shelf-life and supplying the same as a kit.

In the preferred embodiment, a first powdered component of the rapid setting bone cement comprises stabilized dicalcium phosphate dihydrous (DCPD) that contains about 10 ppm to about 60 ppm of magnesium, preferably about 30 ppm to about 50 ppm of magnesium, which is added as a stabilizing agent during the wet chemical precipitation process used to form the stabilized DCPD. This process will be described in detail in the examples below. The source of the magnesium used to stabilize dicalcium phosphate dihydrous is from MgO, $MgO_2$, $Mg(OH)_2$, $MgHPO_4$, $MgHPO_4.3H_2O$, $MgHPO_4.7H_2O$, $Mg_3(PO_4)_2$, $Mg_3(PO_4)_2.4H_2O$, $Mg_3(PO_4)_2.8H_2O$, $Mg_3(PO_4)_2.22H_2O$, $MgCO_3$, $MgCO_3.3H_2O$, $MgCO_3.5H_2O$, $3MgCO_3Mg(OH)_2.3H_2O$, $MgCO_3Mg(OH)_2.3H_2O$, $Mg(C_3H_5O_3)_2.3H_2O$, $MgC_2O_4.2H_2O$, $Mg(C_4H_4O_6)_2.4H_2O$, $MgCO_3.CaCO_3$, $Mg_2P_2O_7$, $Mg(C_{12}H_{23}O_2)_2.2H_2O$, $Mg(C_{14}H_{27}O_2)_2$, $Mg(C_{18}H_{33}O_2)_2$, or $Mg(C_{18}H_{35}O_2)_2$ or a mixture thereof. The preferred source of magnesium to stabilize DCPD is magnesium oxide. The first powdered component may also comprise other calcium phosphate minerals other than dicalcium phosphate dihydrous.

A second powdered component of the rapid setting bone cement comprises at least one calcium phosphate mineral other than the stabilized dicalcium phosphate dihydrous such as tetra-calcium phosphate, di-calcium phosphate, tri-calcium phosphate, mono-calcium phosphate, β-tricalcium phosphate, α-tricalcium phosphate, oxypatite, or hydroxyapatite or a mixture thereof. The preferred calcium phosphate mineral other than the stabilized dicalcium phosphate dihydrous is tetracalcium phosphate (TTCP).

The liquid component of the rapid setting bone cement comprises water and other ionic solution which help setting times. The preferred third liquid component comprises a water-based solution of at least one sodium phosphate and trisodium citrate. Examples of sodium phosphates which can used in the invention are disodium hydrogen phosphate anhydrous, sodium dihydrogen phosphate monohydrate, sodium phosphate monobasic monohydrate, sodium phosphate monobasic dihydrate, sodium phosphate dibasic dihydrate, trisodium phosphate dodecahydrate, or dibasic sodium phosphate heptahydrate, pentasodium tripolyphosphate, sodium metaphosphate, or a mixture thereof. The most preferred third liquid component comprises a water-based solution of disodium hydrogen phosphate anhydrous, sodium dihydrogen phosphate monohydrate and tri-sodium citrate.

In another preferred embodiment, a calcium phosphate cement comprises a powdered first component comprising stabilized dicalcium phosphate dihydrous containing magnesium; a powdered second component comprising at least one calcium phosphate mineral other than said stabilized dicalcium phosphate dihydrous; and a liquid third component comprising water, wherein said cement is storage stable such that said stabilized dicalcium phosphate dihydrous containing magnesium exhibits characteristic x-ray diffraction peaks corresponding to those of dicalcium phosphate dihyrous after 1 year of storage at 25° C. in a sealed container or after an accelerated ageing test of 52 days at 50° C. in a sealed container.

In yet another preferred embodiment, a calcium phosphate cement comprises a powdered first component comprising stabilized dicalcium phosphate dihydrous containing magnesium; a powdered second component comprising at least one calcium phosphate mineral other than said stabilized dicalcium phosphate dihydrous; and a liquid third component comprising water, wherein said cement is storage stable such that said stabilized dicalcium phosphate dihydrous containing magnesium exhibits x-ray diffraction peaks at 11.605, 20,787, 23.391, 26.5, 29.16, 30.484, 31.249, 31.936, 33.538, 34.062, 35.45, 36.34 and 39.67±0.2 degrees two-theta after 1 year of storage at 25° C. in a sealed container or after an accelerated ageing test of 52 days at 50° C. in a sealed container.

In another preferred embodiment, a method for forming a calcium phosphate bone cement comprises: (a) producing a powdered first component comprising stabilized dicalcium phosphate dihydrous containing from about 10 ppm to 60 ppm of magnesium using a wet chemical precipitation process, (b) producing a powdered second component comprising at least one calcium phosphate mineral other than said stabilized dicalcium phosphate dihydrous, and (c) reacting said first and second powdered components with an aqueous liquid component causing a reaction which forms a settable material.

In another preferred embodiment, a method for forming a calcium phosphate bone cement comprises: (a) producing a powdered first component comprising stabilized dicalcium phosphate dihydrous containing magnesium using a wet chemical precipitation process such that said stabilized dicalcium phosphate dihydrous containing magnesium exhibits characteristic x-ray diffraction peaks corresponding to those of dicalcium phosphate dihydrous after 1 year of storage at 25° C. in a sealed container or after an accelerated ageing test of 52 days at 50° C. in a sealed container, (b) producing a powdered second component comprising at least one calcium phosphate mineral other than said stabilized dicalcium phosphate dihydrous, and (c) reacting said first and second powdered components with an aqueous liquid component causing a reaction which forms a settable material.

In yet another preferred embodiment, a kit for forming a calcium phosphate bone cement comprises: (a) a first container containing a mixture of a powdered first component comprising stabilized dicalcium phosphate dihydrous containing from about 10 ppm to 60 ppm of magnesium, and a powdered second component comprising tetra calcium phosphate; and (b) an aqueous liquid component in a second container, wherein the aqueous liquid component comprises at least one sodium phosphate. The aqueous liquid component of the kit may further comprise tri-sodium citrate.

In yet another preferred embodiment, a kit for forming a calcium phosphate bone cement comprises: (a) a first container containing a mixture of a powdered first component comprising stabilized dicalcium phosphate dihydrous containing magnesium such that the x-ray diffraction pattern of said stabilized dicalcium phosphate dihydrous remains substantially the same after 1 year of storage at 25° C. in a sealed container or after an accelerated ageing test of 52 days at 50° C. in a sealed container; and (b) an aqueous liquid component in a second container, wherein the aqueous liquid component comprises at least one sodium phosphate. The aqueous liquid component of the kit may further comprise tri-sodium citrate.

DETAILED DESCRIPTION

This invention is illustrated by, but not limited to, the following examples. Although the following Examples may recite a certain order of steps of making the invention, the invention is not in anyway limited to the order written.

EXAMPLE 1

A. Production of Dicalcium Phosphate Dihydrous with 40 ppm of Magnesium (1) 30% Phosphoric Acid Solution Preparation with 40 ppm Magnesium Addition.

To make the required 30% concentration of orthophosphoric acid ($H_3PO_4$), in a 5 ltr stainless beaker, 261±2 mls of 85% orthophosphoric acid was added to 737±2 mls of deionized water and the beaker was placed on top of a hot plate set to 45° C. Then the temperature probe was placed in the beaker to measure the temperature of the acid solution and the hot plate was turned on to heat the solution to 45° C. The solution was then stirred at a speed of 200±10 rpm to ensure that the probe was measuring a true representation of the beaker content. While the acid solution was being heated to 45° C., 0.0413 grams of magnesium oxide (MgO) (equivalent to about 40 ppm magnesium content or about 0.006883% based on the weight of the DCPD) was added to the solution. Then the pH probes and temperature probes were calibrated and put into the acid solution.

(2) Preparation of Calcium Carbonate Solution 0.45 kg of calcium carbonate ($CaCO_3$) was added into a 5 kg stainless steel beaker and 1 ltr of deionized water was added to the beaker. The beaker was then placed on top of a hot plate which was set to 40° C. Then the temperature probe was placed into the calcium carbonate suspension and the hot plate was turned on. The calcium carbonate suspension was then stirred at a speed of 575±50 rpm to ensure that the probe was measuring a true representation of the beaker content.

(3) Wet Chemical Precipitation

Once the magnesium spiked orthophosphoric acid reached the temperature of 45° C. and calcium carbonate suspension reached the temperature of 40° C., Watson-Marlow's Model 323u/D peristaltic pump system was set up to feed the carbonate suspension into the magnesium spiked orthophosphoric acid at a feed rate of 48±2 ml/min. The pH probe was activated in order to obtain the temperature/pH/time data at the start. Then the carbonate suspension was fed into the acid solution. Once the pH of the acid solution reached a pH of ~3.6, the feed rate of the carbonate suspension was stopped and the pH of the solution was monitored. The pH data from the beginning till the end of the carbonate feed was recorded. Once the pH reached 4.75, the final temperature/pH/time data for the precipitate was recorded and all the temperature and pH probes as well as the peristaltic tube from the solution were removed. The reaction of magnesium, orthophosphoric acid and calcium carbonate produced the stabilized DCPD precipitate.

(4) Precipitate Rinsing

A Whatman #5 filter paper (2.5 μm pore size) was placed into each Buckner funnel attached to a Buckner flask. Five (5) Buckner funnels attached to Buckner flasks were needed per precipitation run. Then, the precipitate solution (approximately 300 ml) was poured into each Buckner funnel attached to a Buckner flask and then a vacuum pump was turned on. The pump drew a vacuum and caused the water to be removed from the precipitate while the filter paper kept the precipitate in the Buckner funnel. After a minimum of two minutes of suction, each Buckner funnel was filled to the rim with deionized water (approx. 200-300 ml) in order to rinse any excess reactants from the precipitate. The precipitate was left under the vacuum for a minimum time of 5 minutes in order to ensure removal of any excessive free moisture.

(5) Freeze Drying

Next, a maximum of 300 grams (approximately half a precipitate production yield) was placed per freeze-drying tray in a manner ensuring that the precipitate is spread out evenly on the tray. The filled trays were then placed into Biopharma Process System's Model VirTis Genesis 25 Super ES freeze dryer. Each tray contained a temperature probe in order to monitor the precipitate temperature/moisture level during drying. Then the freeze dryer cycle was set to the program listed below and was turned on.

TABLE 1

Freeze Drying Recipe For DCPD

| Step | Temperature (° C.) | Time (minutes) | Vacuum (mTorr) |
|---|---|---|---|
| *R | −15 | 1 | 100 |
| **H | −15 | 120 | 100 |
| R | −5 | 120 | 200 |
| H | −5 | 240 | 200 |
| R | 0 | 120 | 1000 |
| H | 0 | 600 | 1000 |
| R | 10 | 60 | 1000 |
| H | 10 | 30 | 1000 |
| R | 20 | 60 | 1000 |
| H | 20 | 30 | 1000 |

*R = Ramp section of the freeze drying cycle.
**H = Hold section of the freeze drying cycle.

Once the precipitate has been dried using the freeze-drying cycle listed in Table 1, the precipitate required milling in order to reduce the average particle size so as to improve the final cement handling and setting properties. This milling is performed using Glen Creston Ltd's Model BM-6 roller ball-mill.

(6) Ball-Milling

3000±30 grams of alumina milling media (13.0 mm diameter×13.2 mm height) was placed into each ball-mill jar. Then, 500+/−25 grams of the dried DCPD precipitates were added into each ball-mill jar and were placed on the ball-mill rollers. The ball-mill was set to 170 rpm and a mill time of 30 minutes, and was turned on.

The ball-mill jar speed was monitored to ensure that it is rotating at 85 rpm. Once the 30 minutes of milling has elapsed, the milling media was separated from the milled powder by sieving through the 8 mm screen provided. The milled and sieved powders have a particle size within a range of about 0.4 to 200 μm, preferably about 35±20 μm, as measured by Beckman Coulter Counter's Model LS 13320 Series particle size analyzer. The milled and sieved powders were then placed into the freeze-drying trays and the freeze-drying procedure as detailed in the previous section was repeated.

B. Production of Tetra Calcium Phosphate (TTCP)

(1) TTCP Cake Preparation

To form the preferred TTCP, the TTCP slurry mixture needs to comprise a 50% w/w solution of solid to liquid with the solid component comprising 60.15% dicalcium phosphate anhydrous (DCPA) and 39.85% $CaCO_3$ and the liquid component comprising purified water. To prepare a batch of TTCP "cakes" for sintering in the furnace, i.e., 3500 grams of TTCP cakes, 2105.25+/−0.5 grams of DCPA was accurately weighed out into a clean 5 liter Buckner flask. To this, 1394.75+/−0.5 grams of $CaCO_3$ were added. To this powder mixture, 3.5 liters of deionized water was added. Table 2 shows the specific amounts and percentages of these components.

TABLE 2

Raw Material Weights For The Production Of TTCP Cakes

| Material | Weight (g) | Ratio (%) |
|---|---|---|
| $CaCO_3$ | 1394.75 ± 1 | 39.85 |
| DCPA | 2105.25 ± 1 | 60.15 |
| Water | 3500.00 ± 10 | 100 |

The Buckner flask was then sealed with appropriate rubber bung and nozzle attachments. The Buckner flask was placed in Glen Creston Ltd's Model T10-B turbular mixer for 20 minutes for homogenous mixing. Table 3 shows the turbular blending parameters.

TABLE 3

Turbular Parameters For Blending Of TTCP Raw Materials

| Parameter | Setting |
|---|---|
| Speed (rpm) | 44 ± 4 |
| Time (mins) | 20 |
| Buckner Flask Volume (%) | 80 |

While the Buckner flask was mixing, the appropriate vacuum tubing to a four-point manifold was connected: one end was attached to the vacuum pump, the other four points were attached to the nozzle attachments on four Buckner flasks. A 9 cm diameter polypropylene Buckner funnel was assembled onto each of the four Buckner flasks, respectively, and Whatman grade 5 filter paper was placed into each Buckner funnel. The blended DCPA/$CaCO_3$/water mixture was removed from the turbular mixer, and the rubber bung was removed. Then, each polypropylene Buckner funnel was completely filled with the TTCP slurry. The TTCP slurry was vacuum dried using the vacuum pump, and the vacuum was drawn for a minimum of 5 minutes until the cakes formed solid top surfaces. Further vacuum drying could be used if required to form solid cakes. Once the cakes were formed, the vacuum on the Buckner flasks was released. Each funnel was removed from the flask and the inverted funnel was gently tapped to remove the cake. Each funnel produced a cake of approximately 300 grams.

Then the spent filter paper was removed, the funnel was washed out with purified water and a fresh filter paper was placed in the funnel. The above steps were repeated until all the slurry solution is in a cake form. The TTCP slurry was hand mixed every four to five cake preparations to ensure homogeneity. If upon removal from the funnel, the cake was broken or has a rough surface, the deionized water was sprayed onto the surface to bind loose fragments together. Any loose remaining fragments were reintroduced to the slurry mixture to form new cakes.

(2) Sintering

All cakes were stacked onto a stainless steel tray and dried for two hours at 200° C. in Lenton's Model AWF 12/42 muffle furnace to drive off excess moisture prior to sintering. The TTCP cakes were now ready to be sintered using the sintering program detailed in Table 4.

TABLE 4

Sintering Parameters For Firing Of TTCP Cakes

| Step | Temperature (° C.) | Time (minutes) | Ramp Rate (° C./min) |
|---|---|---|---|
| Ramp | 800 | 100 | 8 |
| Dwell | 800 | ≧120 | n/a |
| Ramp | 1550 | 94 | 8 |
| Dwell | 1550 | 720 | n/a |
| Cool | 800 | ≦10 | 75 |
| Cool | 20 | 15 | 52 |

The sintered cakes were transferred to a vacuum Buckner flask before the temperature dropped below 150° C. unless the material was to be crushed and milled immediately.

(3) Jaw Crushing

TTCP was processed through Glen Creston's jaw crusher to reduce the granules to a manageable size, preferably in the range of about 2.5 to 7.5 mm prior to processing through the co-mill. The sintered TTCP cakes were manually broken using a mortar and pestle to particle sizes of approximately one inch in diameter before loading into the jaw crusher. In this instance, the jaw crusher gap was set to 5 mm.

(4) Co-Milling of TTCP Granules

TTCP was processed through Quadro Inc.'s co-mill (Model Quadro Comil 197) to reduce the material to the final particle size. The mill speed was set to 5000+/−300 rpm. The impeller gap was set to 0.375" using stainless steel washers. To co-mill the TTCP powder, the jaw-crushed TTCP powders were slowly fed into the co-mill at a rate of approximately 700 grams/min, ensuring that the co-mill did not become clogged with excess powder. (See Table 5 for co-milling parameters.)

TABLE 5

Parameters For Co-Milling The Jaw-Crushed Sintered TTCP Cakes

| Parameter | Setting |
|---|---|
| Screen No. | 0.024" |
| Impeller speed | 5000 rpm |

(5) Ball-Milling

Glen Creston Ltd's Model BM-6 roller ball mill was used to ball-mill the sintered, jaw crushed and co-milled TTCP. The ball milling parameters for the dry milling of the sintered, jaw crushed and co-milled TTCP are listed in Table 6. For the dry milling of the TTCP, a total of 3000±50 grams of alumina milling media (13.0 mm diameter×13.2 mm height) was weighed into an alumina ball-milling jars to which 850 grams of the TTCP was added. The ball mill parameters are outlined in Table 6 below.

TABLE 6

Milling Parameters For The Dry Ball-Milling Of TTCP
TTCP Ball Mill Parameters

| | |
|---|---|
| Speed (rpm) | 85 |
| Time (mins) | 420 |
| Media fill weight (grams) | 3000 +/− 50 |
| TTCP weight (grams) | 850 |

C. Production of Water-Based Solution of Sodium Phosphate and Trisodium Citrate:

Into one liter of high purity water, 22.8 grams of di-sodium hydrogen phosphate anhydrous, 45.5 grams of sodium dihydrogen phosphate monohydrate and 147.1 grams of tri-sodium citrate were added and stirred until they were completely dissolved. The details of this water-based solution are outlined in Table 7 below.

TABLE 7

Liquid Component of Bone Cement

| Chemical Name | Chemical Formula | Mw | Quantity/liter | Molarity |
|---|---|---|---|---|
| Di-Sodium Hydrogen Phosphate Anhydrous | $HNa_2O_4P$ | 141.96 grams | 22.8 g/l | 0.1606 M |
| Sodium Dihydrogen Phosphate Monohydrate | $H_2NaO_4P \cdot H_2O$ | 137.99 grams | 45.5 g/l | 0.3297 M |
| Tri-sodium Citrate | $C_6H_5Na_3O_7 \cdot 2H_2O$ | 294.10 grams | 147.1 g/l | 0.500 M |

D. Mixing of the Powdered Components with the Liquid Component to Produce the Final Cement For the final cement usage, add the DCPD with the TTCP in an equimolar ratio (i.e. DCPD-to-TTCP ratio of 31.97: 68.03). This powder mixture was blended to ensure the formation of a homogeneous mixture. Then the liquid component was added using a liquid-to-powder ratio of 0.32 to form a settable final product.

EXAMPLE 2

A. Production of Dicalcium Phosphate Dihydrous with 60 ppm of Magnesium (1) 30% Phosphoric Acid Solution Preparation with 60 ppm Magnesium Addition To make the required 30% concentration of orthophosphoric acid ($H_3PO_4$), in a 5 ltr stainless beaker, 261±2 mls of 85% orthophosphoric acid was added to 737±2 mls of deionized water and the beaker was placed on top of a hot plate set to 47° C. Then the temperature probe was placed in the beaker to measure the temperature of the acid solution and the hot plate was turned on to heat the solution to 47° C. The solution was then stirred at a speed of 200±10 rpm to ensure that the probe was measuring a true representation of the beaker content. While the acid solution was being heated to 47° C., 0.0620 grams of magnesium oxide (MgO) (equivalent to about 60 ppm magnesium content or about 0.0085% based on the weight of the DCPD) was added to the solution. Then the pH probes and temperature probes were calibrated and put in to the acid solution.

(2) Preparation of Calcium Carbonate Solution 0.45 kg of calcium carbonate ($CaCO_3$) was added into a 5 kg stainless steel beaker and 1 ltr of deionized water was added to the beaker. The beaker was then placed on top of a hot plate which was set to 42° C. Then the temperature probe was placed into the calcium carbonate suspension and the hot plate was turned on. The calcium carbonate suspension was then stirred at a speed of 575+/−50 rpm to ensure that the probe was measuring a true representation of the beaker content.

(3) Wet Chemical Precipitation

Once the magnesium spiked orthophosphoric acid reached the temperature of 47° C. and calcium carbonate suspension reached the temperature of 42° C., Watson-Marlow's Model 323u/D peristaltic system was set up to feed the carbonate suspension into the magnesium spiked orthophosphoric acid at a feed rate of 48+/−2 ml/min. Then the pH probe was activated in order to obtain the temperature/pH/time data at the start. Then the carbonate suspension was fed into the acid solution. Once the pH of the acid solution reached a pH of ~3.6, the feed rate of the carbonate was stopped and the pH of the solution was monitored. The pH data from the beginning till the end of the carbonate feed was recorded. Once the pH reached 5.00, the final temperature/pH/time data for the precipitate was taken and all the temperature and pH probes as well as the peristaltic tube from the solution were removed. The reaction of magnesium, orthophophoric acid and calcium carbonate produced the stabilized DCPD precipitate.

(4) Precipitate Rinsing

A Whatman #5 filter paper (2.5 μm pore size) was placed into each Buckner funnel attached to a Buckner flask. Five (5) Buckner funnels attached to Buckner flasks were needed per precipitation run. Then, the precipitate solution (approximately 300 ml) was poured into each Buckner funnel attached to a Buckner flask and then a vacuum pump was turned on. The pump drew a vacuum and caused the water to be removed from the precipitate while the filter paper kept the precipitate in the Buckner funnel. After a minimum of two minutes of suction, each Buckner funnel was filled to the rim with deionized water (approx. 200-300 ml) in order to rinse any excess reactants from the precipitate. The precipitate was left under the vacuum for a minimum time of 5 minutes in order to ensure removal of any excessive free moisture.

(5) Freeze Drying

Next, a maximum of 300 grams (approximately half a precipitate production yield) was placed per freeze-drying tray in a manner ensuring that the precipitate is spread out evenly on the tray. The filled trays were then placed into Biopharma Process System's Model VirTis Genesis 25 Super ES freeze dryer. Each tray contained a temperature probe in order to monitor the precipitate temperature/moisture level during drying. Then the freeze dryer cycle was set to the program listed below and was turned on.

TABLE 8

Freeze Drying Recipe For DCPD

| Step | Temperature (° C.) | Time (minutes) | Vacuum (mTorr) |
|---|---|---|---|
| *R | −15 | 1 | 100 |
| **H | −15 | 120 | 100 |

TABLE 8-continued

Freeze Drying Recipe For DCPD

| Step | Temperature (° C.) | Time (minutes) | Vacuum (mTorr) |
|---|---|---|---|
| R | −5 | 120 | 200 |
| H | −5 | 240 | 200 |
| R | 0 | 120 | 1000 |
| H | 0 | 600 | 1000 |
| R | 10 | 60 | 1000 |
| H | 10 | 30 | 1000 |
| R | 20 | 60 | 1000 |
| H | 20 | 30 | 1000 |

*R = Ramp section of the freeze drying cycle
**H = Hold section of the freeze drying cycle Once the precipitate has been dried using the freeze-drying cycle listed in Table 8, the precipitate required milling in order to reduce the average particle size so as to improve the final cement handling and setting properties. This milling is performed using Glen Creston's Model BM-6 roller ball-mill.

(6) Ball-Milling

3000+/−30 grams of alumina milling media (13.0 mm diameter×13.2 mm height) was placed into each ball-mill jar. Then, 500+/−25 grams of the dried DCPD precipitates were added into each ball-mill jar and were placed on the ball-mill rollers. The ball-mill was set to 180 rpm and a mill time of 32 minutes, and was turned on.

The ball-mill jar speed was monitored to ensure that it is rotating at 95 rpm. Once the 32 minutes of milling has elapsed, the milling media was separated from the milled powder by sieving through the 8 mm screen provided. The milled and sieved powders have a particle size within a range of about 0.4 to 200 μm, preferably about 35±20 μm, as measured by Beckman Coulter's Model LS 13320 Series particle size analyzer. The milled and sieved powders were then placed into the freeze-drying trays and the freeze-drying procedure as detailed in the previous section was repeated.

B. Production of Tetra Calcium Phosphate (TTCP)

(1) TTCP Cake Preparation

To form the preferred TTCP, the TTCP slurry mixture needs to comprise a 50% w/w solution of solid to liquid with the solid component comprising 60.15% dicalcium phosphate anhydrous (DCPA) and 39.85% $CaCO_3$ and the liquid component comprising purified water. To prepare a batch of TTCP "cakes" for sintering in the furnace, i.e., 3500 grams of TTCP cakes, 2105.25+/−0.5 grams of DCPA was accurately weighed out into a clean 5 liter Buckner flask. To this, 1394.75+/−0.5 grams of $CaCO_3$ were added. To this powder mixture, 3.5 liters of deionized water was added. Table 9 shows the specific amounts and percentages of these components.

TABLE 9

Raw Material Weights For The Production Of TTCP Cakes

| Material | Weight (g) | Ratio (%) |
|---|---|---|
| $CaCO_3$ | 1394.75 ± 1 | 39.85 |
| DCPA | 2105.25 ± 1 | 60.15 |
| Water | 3500.00 ± 10 | 100 |

The Buckner flask was then sealed with appropriate rubber bung and nozzle attachments. The Buckner flask was placed in Glen Creston Ltd's Model T10-B turbular mixer for 25 minutes for homogenous mixing. Table 10 shows the turbular blending parameters.

TABLE 10

Turbular Parameters For Blending Of TTCP Raw Materials

| Parameter | Setting |
|---|---|
| Speed (rpm) | 44 ± 4 |
| Time (mins) | 25 |
| Buckner Flask Volume (%) | 90 |

While the Buckner flask was mixing, the appropriate vacuum tubing to a four-point manifold was connected: one end was attached to the vacuum pump, the other four points were attached to the nozzle attachments on four Buckner flasks. A 9 cm diameter polypropylene Buckner funnel was assembled onto each of the four Buckner flasks, respectively, and Whatman grade 5 filter paper was placed into each Buckner funnel. The blended $DCPA/CaCO_3$/water mixture was removed from the turbular mixer, and the rubber bung was removed. Then, each polypropylene Buckner funnel was completely filled with the TTCP slurry. The TTCP slurry was vacuum dried using the vacuum pump, and the vacuum was drawn for a minimum of 5 minutes until the cakes formed solid top surfaces. Further vacuum drying could be used if required to form solid cakes. Once the cakes were formed, the vacuum on the Buckner flasks was released. Each funnel was removed from the flask and the inverted funnel was gently tapped to remove the cake. Each funnel produced a cake of approximately 300 grams.

Then the spent filter paper was removed, the funnel was washed out with purified water and a fresh filter paper was placed in the funnel. The above steps were repeated until all the slurry solution is in a cake form. The TTCP slurry was hand mixed every four to five cake preparations to ensure homogeneity. If upon removal from the funnel, the cake was broken or has a rough surface, the deionized water was sprayed onto the surface to bind loose fragments together. Any loose remaining fragments were reintroduced to the slurry mixture to form new cakes.

(2) Sintering

All cakes were stacked onto a stainless steel tray and dried for two hours at 200° C. in Lenton's Model AWF 12/42 muffle furnace to drive off excess moisture prior to sintering. The TTCP cakes were now ready to be sintered using the sintering program detailed in Table 11.

TABLE 11

Sintering Parameters For Firing Of TTCP Cakes

| Step | Temperature (° C.) | Time (minutes) | Ramp Rate (° C./min) |
|---|---|---|---|
| Ramp | 800 | 100 | 8 |
| Dwell | 800 | ≧120 | n/a |
| Ramp | 1550 | 94 | 8 |
| Dwell | 1570 | 780 | n/a |
| Cool | 800 | ≦10 | 75 |
| Cool | 20 | 15 | 52 |

The sintered cakes were transferred to a vacuum Buckner flask before the temperature dropped below 150° C. unless the material was to be crushed and milled immediately.

(3) Jaw Crushing

TTCP was processed through Glen Creston's jaw crusher to reduce the granules to a manageable size, preferably in the range of about 2.5 to 7.5 mm prior to processing through the co-mill. The sintered TTCP cakes were manually broken using a mortar and pestle to particle sizes of approximately one inch in diameter before loading into the jaw crusher. In this instance, the jaw crusher gap was set to 7.5 mm.

(4) Co-Milling of TTCP Granules

TTCP was processed through Quadro Inc.'s co-mill (Model Quadro Comil 197) to reduce the material to the final particle size. The mill speed was set to 5500+/−300 rpm. The impeller gap was set to 0.375" using stainless steel washers. To co-mill the TTCP powder, the jaw-crushed TTCP powders were slowly fed into the co-mill at a rate of approximately 700 grams/min, ensuring that the co-mill did not become clogged with excess powder. (See Table 12 for co-milling parameters.)

TABLE 12

Parameters For Co-Milling The Jaw-Crushed Sintered TTCP Cakes

| Parameter | Setting |
|---|---|
| Screen No. | 0.024" |
| Impeller speed | 5500 rpm |

(5) Ball-Milling

Glen Creston Ltd's Model BM-6 roller ball mill was used to ball-mill the sintered, jaw crushed and co-milled TTCP. The ball milling parameters for the dry milling of the sintered, jaw crushed and co-milled TTCP are listed in Table 13. For the dry milling of the TTCP, a total of 3000+/−50 grams of alumina milling media (13.0 mm diameter×13.2 mm height) was weighed into an alumina ball-milling jar, to which 900 grams of the TTCP was added. The ball mill parameters are outlined in Table 13 below.

TABLE 13

Milling Parameters For The Dry Ball-Milling Of TTCP
TTCP Ball Mill Parameters

| Speed (rpm) | 95 |
|---|---|
| Time (mins) | 430 |
| Media fill weight (grams) | 3000 +/− 50 |
| TTCP weight (grams) | 900 |

C. Production of Water-Based Solution of Sodium Phosphate and Trisodium Citrate

Into one liter of high purity water, 22.8 grams of di-sodium hydrogen phosphate anhydrous, 45.5 grams of sodium dihydrogen phosphate monohydrate and 147.1 grams of tri-sodium citrate were added and stirred until they were completely dissolved. The details of this water-based solution are outlined in Table 14 below.

TABLE 14

Liquid Component of Bone Cement

| Chemical Name | Chemical Formula | Mw | Quantity/liter | Molarity |
|---|---|---|---|---|
| Di-Sodium Hydrogen Phosphate Anhydrous | $HNa_2O_4P$ | 141.96 grams | 22.8 g/l | 0.1606 M |

TABLE 14-continued

Liquid Component of Bone Cement

| Chemical Name | Chemical Formula | Mw | Quantity/liter | Molarity |
|---|---|---|---|---|
| Sodium Dihydrogen Phosphate Monohydrate | $H_2NaO_4P \cdot H_2O$ | 137.99 | 45.5 g/l grams | 0.3297 M |
| Tri-sodium Citrate | $C_6H_5Na_3O_7 \cdot 2H_2O$ | 294.10 | 147.1 g/l grams | 0.500 M |

D. Mixing of the Powdered Components with the Liquid Component to Produce the Final Cement For the final cement usage, add the DCPD with the TTCP in an equimolar ratio (i.e. DCPD-to-TTCP ratio of 31.97:68.03). This powder mixture was blended to ensure the formation of a homogeneous mixture. Then the liquid component was added using a liquid-to-powder ratio of 0.32 to form a settable final product.

Figure 1:
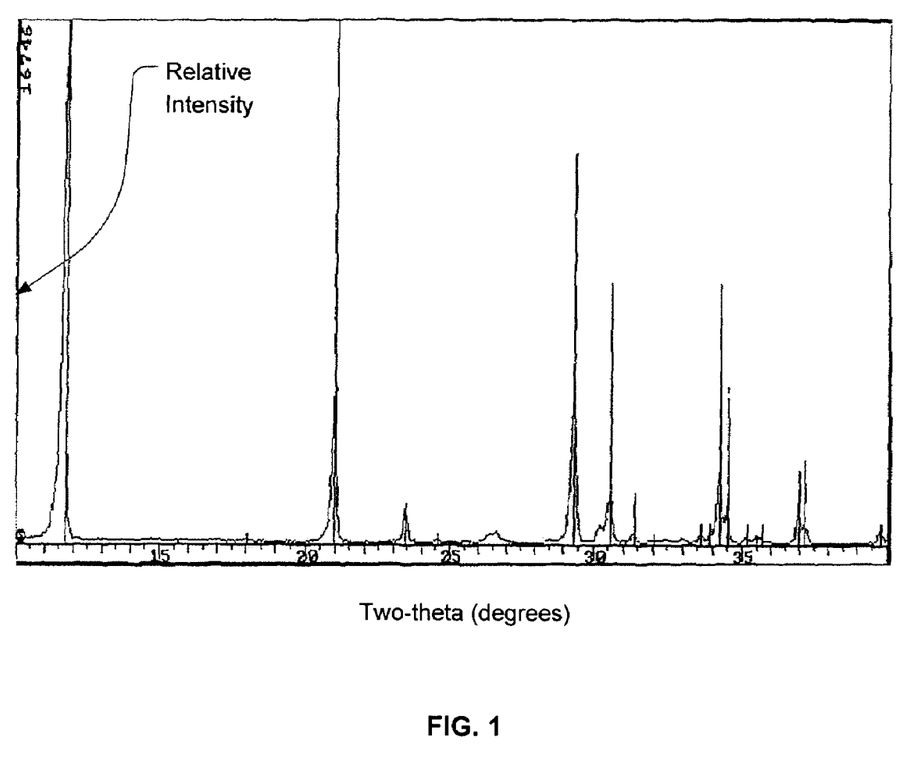
FIG. 1 is a characteristic X-ray powder diffraction pattern of DCPD containing 40 ppm of magnesium before the accelerated ageing test.
Figure 3:
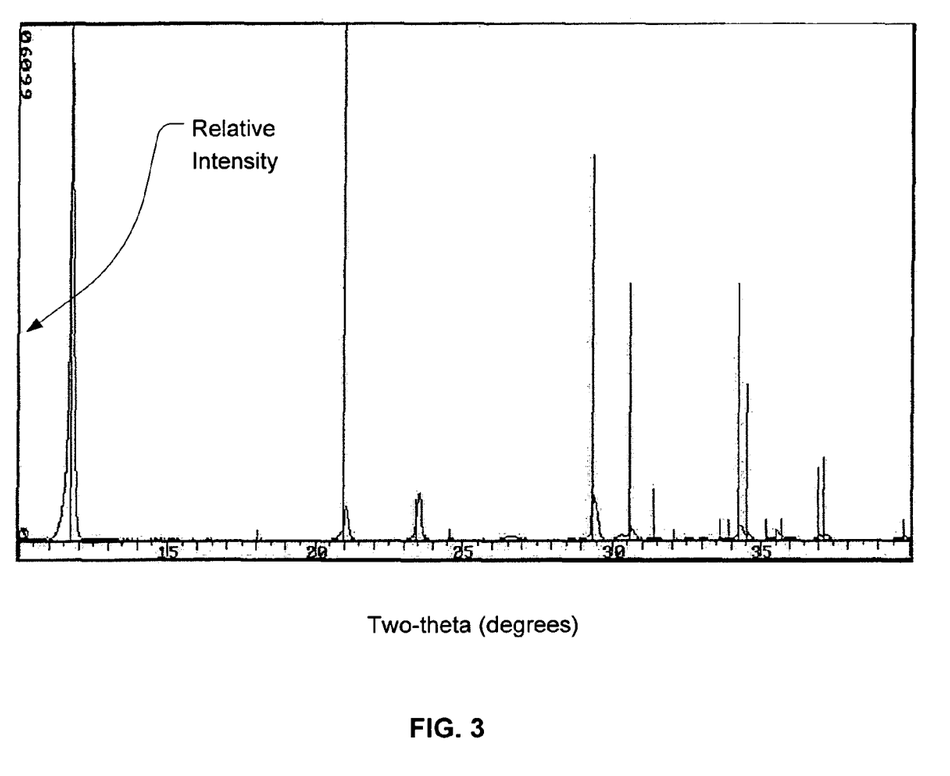
FIG. 3 is a characteristic X-ray powder diffraction pattern of DCPD containing 60 ppm of magnesium before the accelerated ageing test.

The DCPD powders produced as described in Examples 1 and 2 were analyzed for long-term stability using an X-ray diffractometer. First, as shown in FIGS. 1 and 3, the X-ray powder diffraction patterns of the initial dry DCPD powders of Example 1 and Example 2 were collected using Rigaku's X-ray diffractometer.

Then, 5 grams of DCPD powders were packaged in a topaz bowl and heat-sealed with a breathable Tyvek lid. This bowl is then placed in a foil pouch with 10 grams of silicon desiccant. The foil pouch is then heat-sealed. The sealed foil pouch is then placed in a climatic oven set at 50° C. and aged for a set period of time. It has been determined that storage under these conditions for 52 days is equivalent to 1 year real time ageing.

The DCPD powders of Example 1 were stored in a climatic oven set at 50° C. for 77 days, and the DCPD powders of Example 2 were stored in a climatic oven set at 50° C. for 91 days for accelerated ageing tests.

Figure 2:
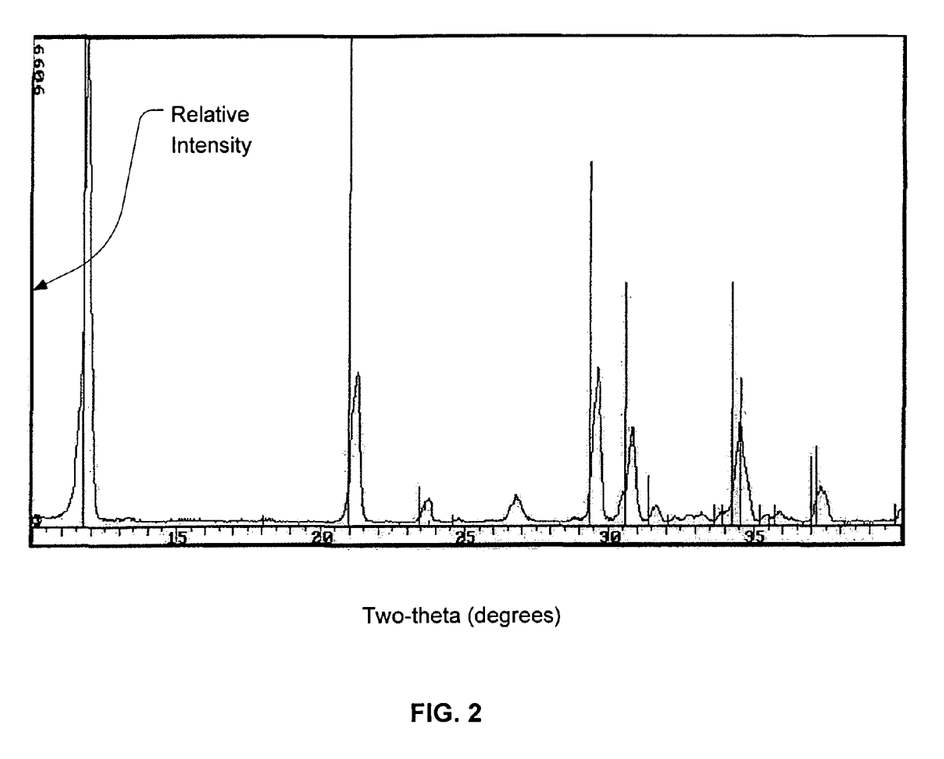
FIG. 2 is a characteristic X-ray powder diffraction pattern of DCPD containing 40 ppm of magnesium after the accelerated ageing test (i.e., after storage at 50° C. for 77 days).
Figure 4:
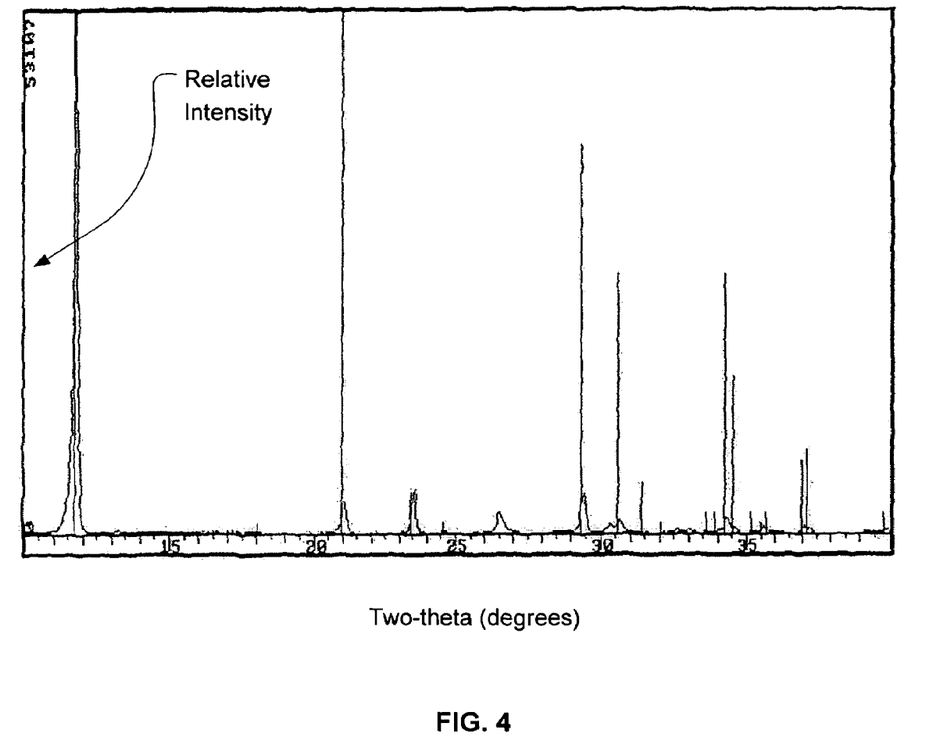
FIG. 4 is a characteristic X-ray powder diffraction pattern of DCPD containing 60 ppm of magnesium after the accelerated ageing test (i.e., after storage at 50° C. for 90 days).

After the exposure in the accelerated ageing test conditions, the X-ray powder diffraction patterns of the DCPD powders of Example 1 and Example 2 were collected again using the same Rigaku's X-ray diffractometer. As shown in FIGS. 2 and 4, said stabilized dicalcium phosphate dihydrous containing magnesium exhibited characteristic x-ray diffraction peaks of dicalcium phosphate dihydrous. More specifically, after the exposure in the accelerated ageing test conditions as mentioned above, the X-ray powder diffraction patterns of the DCPD powders of Example 1 and Example 2, said stabilized DCPD powders exhibited x-ray diffraction peaks at 11.605, 20,787, 23.391, 26.5, 29.16, 30.484, 31.249, 31.936, 33.538, 34.062, 35.45, 36.34 and 39.67±0.2 degrees two-theta after 1 year of storage at 25° C. in a sealed container or after an accelerated ageing test of 52 days at 50° C. in a sealed container.

The bone cements produced as described in Examples 1 and 2 were also tested for penetration resistance after the accelerated ageing tests. The preferred penetration resistance requirements for the present invention are $\geq$1000 psi after 5 minutes from being mixed and a resistance of $\geq$3500 psi after 10 minutes from being mixed. Tables 15 and 16 show the results of the penetration resistance tests using the bone cements produced according to Examples 1 and 2 above.

TABLE 15

Penetration Resistance Test Results
Bone Cement Containing DCPD With
40 ppm Of Magnesium (Example 1)

| Sample Number | Results |
|---|---|
| 1 | 3414 psi @ 5 min |
|   | 7227 psi @ 10 min |
| 2 | 3723 psi @ 5 min |
|   | 6843 psi @ 10 min |
| 3 | 2441 psi @ 5 min |
|   | 7444 psi @ 10 min |
| 4 | 2615 psi @ 5 min |
|   | 6606 psi @ 10 min |
| 5 | 2193 psi @ 5 min |
|   | 6243 psi @ 10 min |
| 6 | 2341 psi @ 5 min |
|   | 7153 psi @ 10 min |
| Sample Average | 2788 psi @ 5 min |
|   | 6919 psi @ 10 min |

TABLE 16

Penetration Resistance Test Results
Bone Cement Containing DCPD With
60 ppm Of Magnesium (Example 2)

| Sample Number | Results |
|---|---|
| 1 | 1947 psi @ 5 min |
|   | 4668 psi @ 10 min |
| 2 | 1675 psi @ 5 min |
|   | 3947 psi @ 10 min |
| 3 | 1649 psi @ 5 min |
|   | 4567 psi @ 10 min |
| 4 | 2371 psi @ 5 min |
|   | 3047 psi @ 10 min |
| 5 | 2096 psi @ 5 min |
|   | 5872 psi @ 10 min |
| 6 | 2903 psi @ 5 min |
|   | 5483 psi @ 10 min |
| Sample Average | 2106 psi @ 5 min |
|   | 4930 psi @ 10 min |

As these and other variations and combinations of the features discussed above can be utilized without departing from the present invention as defined by the claims, the foregoing description of the preferred embodiments should be taken by way of illustration rather than by way of limitation of the invention as defined by the claims.

The invention claimed is:

1. A calcium phosphate cement comprising:
   (a) a powdered first component comprising stabilized dicalcium phosphate dihydrous containing from about 10 ppm to about 60 ppm of magnesium,
   (b) a powdered second component comprising at least one calcium phosphate mineral other than said stabilized dicalcium phosphate dihydrous, and
   (c) a liquid third component comprising water.

2. The calcium phosphate cement of claim 1, wherein said stabilized dicalcium phosphate dihydrous is produced using a wet chemical precipitation process.

3. The calcium phosphate cement of claim 1, wherein said magnesium is present in an amount from about 30 ppm to about 50 ppm of magnesium.

4. The calcium phosphate cement of claim 1, wherein said at least one calcium phosphate mineral other than said stabilized dicalcium phosphate dihydrous is tetracalcium phosphate, dicalcium phosphate, tricalcium phosphate, monocalcium phosphate, oxyapatite, or hydroxypatite or a mixture thereof.

5. The calcium phosphate cement of claim 4, wherein said calcium phosphate mineral other than said stabilized dicalcium phosphate dihydrous is tetracalcium phosphate.

6. The calcium phosphate cement of claim 1, wherein the source of said magnesium used to stabilize dicalcium phosphate dihydrous is from $MgO$, $MgO_2$, $Mg(OH)_2$, $MgHPO_4$, $MgHPO_4.3H_2O$, $MgHPO_4.7H_2O$, $Mg_3(PO_4)_2$, $Mg_3(PO_4)_2.4H_2O$, $Mg_3(PO_4)_2.8H_2O$, $Mg_3(PO_4)_2.22H_2O$, $MgCO_3$, $MgCO_3.3H_2O$, $MgCO_3.5H_2O$, $3MgCO_3Mg(OH)_2.3H_2O$, $MgCO_3Mg(OH)_2.3H_2O$, $Mg(C_3H_5O_3)_2.3H_2O$, $MgC_2O_4.2H_2O$, $Mg(C_4H_4O_6)_2.4H_2O$, $MgCO_3.CaCO_3$, $Mg_2P_2O_7$, $Mg(C_{12}H_{23}O_2)_2.2H_2O$, $Mg(C_{14}H_{27}O_2)_2$, $Mg(C_{18}H_{33}O_2)_2$, or $Mg(C_{18}H_{35}O_2)_2$ or a mixture thereof.

7. The calcium phosphate cement of claim 6, wherein the source of said magnesium used to stabilize dicalcium phosphate dihydrous is magnesium oxide.

8. The calcium phosphate cement of claim 1, wherein said third liquid component further comprises at least one sodium phosphate.

9. The calcium phosphate cement of claim 8, wherein said at least one sodium phosphate is di-sodium hydrogen phosphate anhydrous, sodium dihydrogen phosphate monohydrate, sodium phosphate monobasic monohydrate, sodium phosphate monobasic dihydrate, sodium phosphate dibasic dihydrate, trisodium phosphate dodecahydrate, or dibasic sodium phosphate heptahydrate, pentasodium tripolyphosphate, sodium metaphosphate, or a mixture thereof.

10. The phosphate cement of claim 8, wherein said third liquid component further comprises tri-sodium citrate.

11. A method for forming a calcium phosphate bone cement comprising:
(a) producing a powdered first component comprising stabilized dicalcium phosphate dihydrous containing from about 10 ppm to 60 ppm of magnesium using a wet chemical precipitation process,
(b) producing a powdered second component comprising at least one calcium phosphate mineral other than said stabilized dicalcium phosphate dihydrous, and
(c) reacting said first and second powdered components with an aqueous liquid component causing a reaction which forms a settable material.

12. The method for forming a calcium phosphate bone cement of claim 11, wherein said reacting is performed by first blending said first and second powdered components to form a homogeneous mixture, then mixing said homogeneous mixture of said first and second powdered components with said aqueous liquid component causing a reaction which forms a settable material.

13. The method for forming a calcium phosphate bone cement of claim 11, wherein said at least one calcium phosphate mineral other than said stabilized dicalcium phosphate dihydrous is tetracalcium phosphate, dicalcium phosphate, tricalcium phosphate, monocalcium phosphate, oxyapatite, or hydroxypatite or a mixture thereof.

14. The method for forming a calcium phosphate bone cement of claim 13, wherein at least one said calcium phosphate mineral other than said stabilized dicalcium phosphate dihydrous is tetracalcium phosphate.

15. The method for forming a calcium phosphate bone cement of claim 11, wherein the source of said magnesium is from $MgO$, $MgO_2$, $Mg(OH)_2$, $MgHPO_4$, $MgHPO_4.3H_2O$, $MgHPO_4.7H_2O$, $Mg_3(PO_4)_2$, $Mg_3(PO_4)_2.4H_2O$, $Mg_3(PO_4)_2.8H_2O$, $Mg_3(PO_4)_2.22H_2O$, $MgCO_3$, $MgCO_3.3H_2O$, $MgCO_3.5H_2O$, $3MgCO_3Mg(OH)_2.3H_2O$, $MgCO_3Mg(OH)_2.3H_2O$, $Mg(C_3H_5O_3)_2.3H_2O$, $MgC_2O_4.2H_2O$, $Mg(C_4H_4O_6)_2.4H_2O$, $MgCO_3.CaCO_3$, $Mg_2P_2O_7$, $Mg(C_{12}H_{23}O_2)_2.2H_2O$, $Mg(C_{14}H_{27}O_2)_2$, $Mg(C_{18}H_{33}O_2)_2$, or $Mg(C_{18}H_{35}O_2)_2$ or a mixture thereof.

16. The method for forming a calcium phosphate bone cement of claim 15, wherein the source of said magnesium used to stabilize dicalcium phosphate dihydrous is magnesium oxide.

17. The method for forming a calcium phosphate bone cement of claim 11, wherein said third liquid component further comprises at least one sodium phosphate.

18. The method for forming a calcium phosphate bone cement of claim 17, wherein said at least one sodium phosphate is di-sodium hydrogen phosphate anhydrous, sodium dihydrogen phosphate monohydrate, sodium phosphate monobasic monohydrate, sodium phosphate monobasic dihydrate, sodium phosphate dibasic dihydrate, trisodium phosphate dodecahydrate, or dibasic sodium phosphate heptahydrate, pentasodium tripolyphosphate, sodium metaphosphate, or a mixture thereof.

19. The method for forming a calcium phosphate bone cement of claim 17, wherein said third liquid component further comprises tri-sodium citrate.

20. A kit for forming a calcium phosphate bone cement comprising:
(a) a first container containing a mixture of a powdered first component comprising stabilized dicalcium phosphate dihydrous containing from about 10 ppm to 60 ppm of magnesium, and a powdered second component comprising tetra calcium phosphate; and
(b) an aqueous liquid component in a second container, wherein said aqueous liquid component comprises at least one sodium phosphate.

21. The kit for forming a calcium phosphate bone cement of claim 20, wherein said aqueous liquid component further comprises tri-sodium citrate.

22. A calcium phosphate cement comprising:
(a) a powdered first component comprising stabilized dicalcium phosphate dihydrous containing magnesium,
(b) a powdered second component comprising at least one calcium phosphate mineral other than said stabilized dicalcium phosphate dihydrous, and
(c) a liquid third component comprising water, wherein said cement is storage stable such that said stabilized dicalcium phosphate dihydrous containing magnesium exhibits characteristic x-ray diffraction peaks corresponding to those of dicalcium phosphate dihydrous after 1 year of storage at 25° C. in a sealed container or after an accelerated ageing test of 52 days at 50° C. in a sealed container.

23. The calcium phosphate cement of claim 21, wherein said stabilized dicalcium phosphate dihydrous containing magnesium exhibits x-ray diffraction peaks at 11.605, 20,787, 23.391, 26.5, 29.16, 30.484, 31.249, 31.936, 33.538, 34.062, 35.45, 36.34 and 39.67±0.2 degrees two-theta after 1 year of storage at 25° C. in a sealed container or after an accelerated ageing test of 52 days at 50° C. in a sealed container.

24. The calcium phosphate cement of claim 22, wherein said stabilized dicalcium phosphate dihydrous is produced using a wet chemical precipitation process.

25. The calcium phosphate cement of claim 22, wherein said magnesium is present in an amount from about 10 ppm to about 60 ppm of magnesium.

26. The calcium phosphate cement of claim 25, wherein said magnesium is present in an amount from about 30 ppm to about 50 ppm of magnesium.

27. The calcium phosphate cement of claim 22, wherein said at least one calcium phosphate mineral other than said stabilized dicalcium phosphate dihydrous is tetracalcium phosphate, dicalcium phosphate, tricalcium phosphate, monocalcium phosphate, oxyapatite, or hydroxypatite or a mixture thereof.

28. The calcium phosphate cement of claim 27, wherein said calcium phosphate mineral other than said stabilized dicalcium phosphate dihydrous is tetracalcium phosphate.

29. The calcium phosphate cement of claim 22, wherein the source of said magnesium used to stabilize dicalcium phosphate dihydrous is from $MgO$, $MgO_2$, $Mg(OH)_2$, $MgHPO_4$, $MgHPO_4.3H_2O$, $MgHPO_4.7H_2O$, $Mg_3(PO_4)_2$, $Mg_3(PO_4)_2.4H_2O$, $Mg_3(PO_4)_2.8H_2O$, $Mg_3(PO_4)_2.22H_2O$, $MgCO_3$, $MgCO_3.3H_2O$, $MgCO_3.5H_2O$, $3MgCO_3Mg(OH)_2.3H_2O$, $MgCO_3Mg(OH)_2.3H_2O$, $Mg(C_3H_5O_3)_2.3H_2O$, $MgC_2O_4.2H_2O$, $Mg(C_4H_4O_6)_2.4H_2O$, $MgCO_3.CaCO_3$, $Mg_2P_2O_7$, $Mg(C_{12}H_{23}O_2)_2.2H_2O$, $Mg(C_{14}H_{27}O_2)_2$, $Mg(C_{18}H_{33}O_2)_2$, or $Mg(C_{18}H_{35}O_2)_2$ or a mixture thereof.

30. The calcium phosphate cement of claim 29, wherein the source of said magnesium used to stabilize dicalcium phosphate dihydrous is magnesium oxide.

31. The calcium phosphate cement of claim 22, wherein said third liquid component further comprises at least one sodium phosphate.

32. The calcium phosphate cement of claim 31, wherein said at least one sodium phosphate is di-sodium hydrogen phosphate anhydrous, sodium dihydrogen phosphate monohydrate, sodium phosphate monobasic monohydrate, sodium phosphate monobasic dihydrate, sodium phosphate dibasic dihydrate, trisodium phosphate dodecahydrate, or dibasic sodium phosphate heptahydrate, pentasodium tripolyphosphate, sodium metaphosphate, or a mixture thereof.

33. The phosphate cement of claim 32, wherein said third liquid component further comprises tri-sodium citrate.

34. A method for forming a calcium phosphate bone cement comprising:
  (a) producing a powdered first component comprising stabilized dicalcium phosphate dihydrous containing magnesium using a wet chemical precipitation process such that said stabilized dicalcium phosphate dihydrous containing magnesium exhibits characteristic x-ray diffraction peaks corresponding to those of dicalcium phosphate dihydrous after 1 year of storage at 25° C. in a sealed container or after an accelerated ageing test of 52 days at 50° C. in a sealed container,
  (b) producing a powdered second component comprising at least one calcium phosphate mineral other than said stabilized dicalcium phosphate dihydrous, and
  (c) reacting said first and second powdered components with an aqueous liquid component causing a reaction which forms a settable material.

35. The method for forming a calcium phosphate bone cement of claim 34, wherein said characteristic x-ray diffraction peaks corresponding to those of dicalcium phosphate dihydrous containing magnesium exhibits x-ray diffraction peaks at 11.605, 20,787, 23.391, 26.5, 29.16, 30.484, 31.249, 31.936, 33.538, 34.062, 35.45, 36.34 and 39.67±0.2 degrees two-theta after 1 year of storage at 25° C. in a sealed container or after an accelerated ageing test of 52 days at SOW in a sealed container.

36. A method for forming a calcium phosphate bone cement of claim 34, wherein said reacting is performed by first blending said first and second powdered components to form a homogeneous mixture, then mixing said homogeneous mixture of said first and second powdered components with said aqueous liquid component causing a reaction which forms a settable material.

37. A kit for forming a calcium phosphate bone cement comprising:
  (a) a first container containing a mixture of a powdered first component comprising stabilized dicalcium phosphate dihydrous containing magnesium such that the X-ray diffraction pattern of said stabilized dicalcium phosphate dihydrous remains substantially the same after 1 year of storage at 25° C. in a sealed container or after an accelerated ageing test of 52 days at 50° C. in a sealed container; and
  (b) an aqueous liquid component in a second container, the liquid component comprising at least one sodium phosphate.

38. The kit for forming a calcium phosphate bone cement of claim 37, wherein said aqueous liquid component further comprises tri-sodium citrate.

* * * * *

UNITED STATES PATENT AND TRADEMARK OFFICE
CERTIFICATE OF CORRECTION

PATENT NO. : 7,416,602 B2 Page 1 of 1
APPLICATION NO. : 11/102254
DATED : August 26, 2008
INVENTOR(S) : Matthew E. Murphy et al.

It is certified that error appears in the above-identified patent and that said Letters Patent is hereby corrected as shown below:

Column 18, line 17, "52 days at SOW" should read -- 52 days at 50 °C --.
Column 18, line 34, "52 days at 50 °C. in" should read -- 52 days at 50 °C in --.

Signed and Sealed this

Thirtieth Day of March, 2010

David J. Kappos
*Director of the United States Patent and Trademark Office*